United States Patent
Choy et al.

(10) Patent No.: US 9,295,462 B2
(45) Date of Patent: Mar. 29, 2016

(54) SUTURE COMPRISING DRUG-LOADED POLYMER LAYER AND METHOD OF MANUFACTURING THE SAME

(75) Inventors: Young Bin Choy, Seongnam-si (KR); Chan Yeong Heo, Yongin-si (KR); Ji Eun Lee, Incheon (KR); Su Bin Park, Seoul (KR)

(73) Assignee: SNU R&DB FOUNDATION, Seoul (KR)

(*) Notice: Subject to any disclaimer, the term of this patent is extended or adjusted under 35 U.S.C. 154(b) by 294 days.

(21) Appl. No.: 13/304,460

(22) Filed: Nov. 25, 2011

(65) Prior Publication Data
US 2012/0303057 A1 Nov. 29, 2012

(30) Foreign Application Priority Data
May 24, 2011 (KR) .................. 10-2011-0049218

(51) Int. Cl.
*A61B 17/06* (2006.01)
*A61L 17/00* (2006.01)
*A61L 17/14* (2006.01)
*A61B 17/00* (2006.01)

(52) U.S. Cl.
CPC ......... *A61B 17/06166* (2013.01); *A61L 17/005* (2013.01); *A61L 17/145* (2013.01); *A61B 2017/00526* (2013.01); *A61B 2017/00893* (2013.01)

(58) Field of Classification Search
CPC ............... A61B 17/06166; A61B 2017/00893; A61B 2017/00004; A61B 2017/00526; A61L 17/005; A61L 17/06
USPC .................................................. 606/228–231
See application file for complete search history.

(56) References Cited

U.S. PATENT DOCUMENTS

| 3,791,388 | A | * | 2/1974 | Hunter et al. | 606/229 |
| 4,712,553 | A | * | 12/1987 | MacGregor | 606/231 |
| 6,878,757 | B2 | | 4/2005 | Roby | |
| 2005/0084514 | A1 | * | 4/2005 | Shebuski et al. | 424/426 |
| 2011/0112513 | A1 | * | 5/2011 | Hester et al. | 604/514 |

FOREIGN PATENT DOCUMENTS

WO   WO 2005/055836 A2   6/2005

OTHER PUBLICATIONS

Zurita, Puiggali, Rodriguea-Galan Micromolecular Bioscience, Wiley-VCH Verlag GmbH & Co. KGaA, Weinheim.

* cited by examiner

*Primary Examiner* — Sarah W Aleman
(74) *Attorney, Agent, or Firm* — Benjamin Aaron Adler

(57) ABSTRACT

This invention relates to a suture including a drug-loaded polymer layer and a method of manufacturing the same, and more particularly, to a suture, the surface of which is wound with a film including a drug-loaded biodegradable polymer layer, or coated with a drug-loaded biodegradable polymer layer, and to a method of manufacturing the same.

12 Claims, 5 Drawing Sheets

FIG. 3
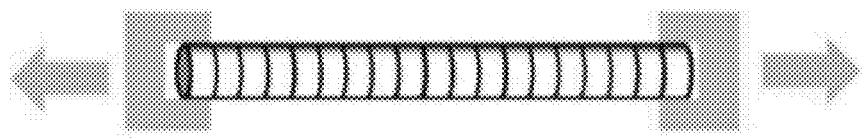

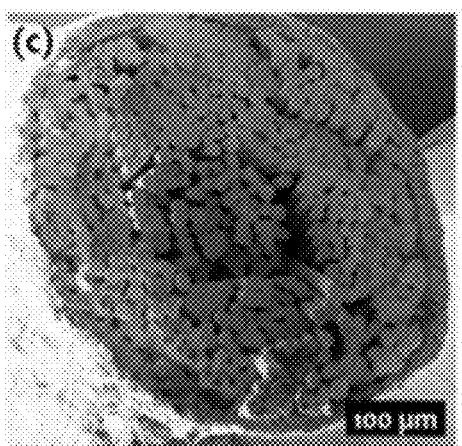
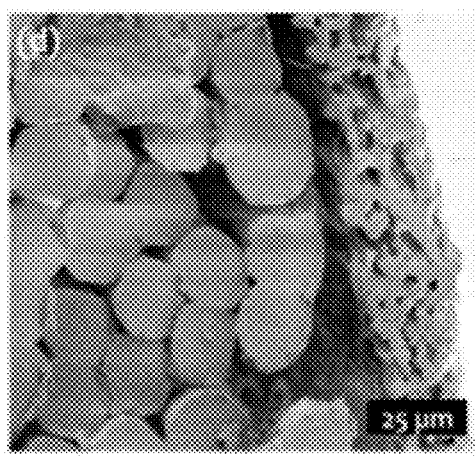
FIG. 4C      FIG. 4D

SUTURE COMPRISING DRUG-LOADED POLYMER LAYER AND METHOD OF MANUFACTURING THE SAME

CROSS-REFERENCE TO RELATED APPLICATIONS

This nonprovisional application claims benefit of priority under 35 U.S.C. §119(a) of pending Korean Application Serial No. 10-2011-0049218, filed May 24, 2011, the entirety of which is hereby incorporated by reference.

BACKGROUND OF THE INVENTION

1. Field of the Invention

The present invention relates to a suture comprising a drug-loaded polymer layer and a method of manufacturing the same, and more particularly, to a suture the surface of which is covered with film including a drug-loaded biodegradable polymer layer, or coated with a drug-loaded biodegradable polymer layer, and to a method of manufacturing the same.

2. Description of the Related Art

Sutures, which are necessary for sewing excised or incised sites during surgical operation, are a medical device for tying or binding tissue such as blood vessels, etc. Sutures are classified into non-absorbable sutures and absorbable sutures. Non-absorbable sutures are mainly used to sew tissue exposed to the outside, which can retain tensile strength for longer than the period of healing. Dissimilarly, for sewing internal organs, absorbable sutures are mainly used, which are biodegraded and absorbed by water or enzyme, avoiding the need of secondary anesthesia and operation to remove the sutures.

To avoid or minimize any complications at the sutured sites after a surgical operation, an anti-inflammatory or antibiotic drug is often orally administered. However, this method may not be effective because the drug would be delivered not only to the sites of interest but systemically to the whole body. Additionally, long term administration of an oral drug may cause a great deal of inconvenience and possible complications to patients.

Although many researchers have studied sutures in which drug is directly loaded, disadvantages exist in these studies in terms of the weakened mechanical strength, limited amount of the loaded drug, and inability to control drug delivery.

Specifically, R. Zurita et al. developed a method of loading ibuprofen as a model drug on conventional monofilament or multifilament absorbable sutures (*Macromolecular Bioscience*, 2006, 6, 767-775). In this article, the drug release profiles are varied with preparing conditions and the mechanical properties thereof are grasped, which resulted in the finding that the sutures coated by immersion in a solution including a drug and a polymer exhibited the undesirably decreased mechanical strength and limited amount of the loaded drug.

U.S. Pat. No. 6,878,757 discloses a suture coated with a mixture comprising antibiotics and a copolymer obtained by adding a small amount of monomer having a variety of functional groups to a large amount of ε-caprolactone. This patent is also problematic because the suture directly coated with the solution of polymer and drug exhibited the decrease in mechanical strength.

US Patent Application Publication No. 2004040488 discloses a suture having pores or channels in which a liquid drug is loaded, so that the liquid drug is delivered to the wound. This patent is also problematic because the tube-shaped suture, provided in the form of the drug being contained therein, undesirably decreased the mechanical strength.

Meanwhile, the drug-delivery sutures that are currently in clinical use are limited to the use in preventing infection, thereby only with the drugs, such as antibiotics. Therefore, it is necessary to develop sutures enabled with delivery of various types of drugs for many different purposes.

Given these, the present inventors have discovered a system composed of a biodegradable material, which can be loaded with diverse types of drugs, such as an anticancer agent, anti-inflammatory drug, antibiotic, etc. The system in turn, is physically adhered to the suture to ensure topical transfer of the drug, thereby improving therapeutic effects, which culminated in the present invention.

SUMMARY OF THE INVENTION

Therefore, an object of the present invention is to provide a suture comprising a drug-loaded biodegradable polymer layer.

Another object of the present invention is to provide a method of manufacturing a suture comprising a drug-loaded biodegradable polymer layer.

In order to accomplish the above objects, an aspect of the present invention provides a suture comprising a suture and a layer applied on the suture, wherein the layer is a drug-loaded biodegradable polymer layer.

Another aspect of the present invention provides a method of manufacturing a suture, comprising 1) preparing a film including a drug-loaded biodegradable polymer layer and 2) winding the film including the drug-loaded biodegradable polymer layer around the surface of a suture.

A further aspect of the present invention provides a method of manufacturing a suture, comprising 1) preparing a mixture comprising a drug and a biodegradable polymer and 2) coating the surface of a suture with the mixture including the drug in a non-wet manner, thus forming a drug-loaded biodegradable polymer layer.

BRIEF DESCRIPTION OF THE DRAWINGS

The above and other objects, features and advantages of the present invention will be more clearly understood from the following detailed description taken in conjunction with the accompanying drawings, in which:

FIG. 3 schematically shows a pulling process that adheres the suture wound with the drug carrier by heat;

FIGS. 4C and 4D are scanning electron microscope (SEM) images showing the cross-section of the DS suture (FIG. 4C: magnification of ×200, FIG. 4D: magnification of ×1000);

DESCRIPTION OF SPECIFIC EMBODIMENTS

The present invention provides a suture comprising a drug-loaded biodegradable polymer layer.

In a preferred embodiment, the present invention provides a suture comprising a suture and a layer applied on the suture, wherein the layer is a drug-loaded biodegradable polymer layer.

As used herein, the term "suture" means a medical device that is used to tie or bind tissue such as blood vessels or the like in order to sew the excised or incised sites upon conducting a surgical operation.

Conventional drug delivery sutures are prepared by coating the suture with a solution containing a drug such as an anti-inflammatory drug or an antibiotic agent so as to relieve pain or minimize the chance of infection at the sewed site, respectively, after conducting a surgical operation or to prevent the site operated on from festering. As such, the coating is applied by immersing the suture in the solution containing the drug, so that the drug infiltrates the suture and may thus affect the suture itself, undesirably deteriorating the mechanical strength of the suture.

The suture according to the present invention is embodied so as to enable the delivery of a drug without lowering its mechanical strength, by separately preparing a film including a drug-loaded biodegradable polymer layer and then winding it around the surface of the suture, or by directly coating the surface of the suture with a drug-loaded biodegradable polymer layer in a non-wet manner.

Figure 1:
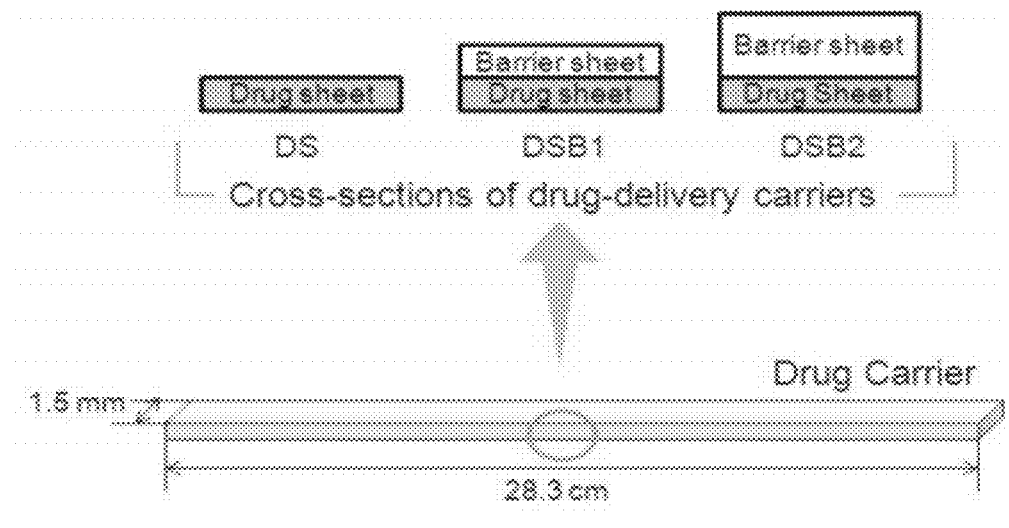
FIG. 1 schematically shows a process of preparing a drug-loaded biodegradable polymer film (which is a drug carrier) according to the present invention, in which DS is a drug-loaded biodegradable polymer film composed exclusively of the drug sheet, DSB1 is a drug-loaded biodegradable polymer film consisted of the drug sheet and the barrier sheet formed thereon using electrospinning for 100 min, and DSB2 is a drug-loaded biodegradable polymer film composed of the drug sheet and the barrier sheet formed thereon using electrospinning for 200 min.
Figure 2:
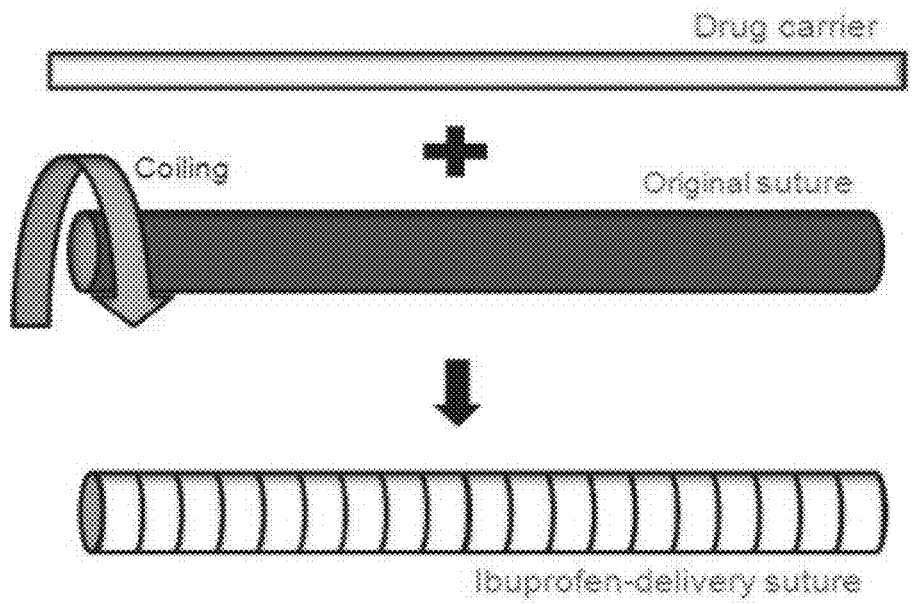
FIG. 2 schematically shows a process of winding the drug carrier around the surface of a suture.

In the present invention, the process of winding the surface of the suture with the film may be performed as shown in FIGS. 1 and 2.

As shown in FIG. 1, a film, which includes a drug-loaded biodegradable polymer layer (which is a drug sheet), is prepared, cut at a predetermined interval, and then wound around the surface of a suture as an original suture as seen in FIG. 2. The film may be closely wound without overlapping itself on the surface of the suture, but the present invention is not limited thereto.

In the present invention, the film including the drug-loaded biodegradable polymer layer may be composed of the drug-loaded biodegradable polymer layer alone, or of the drug-loaded biodegradable polymer layer and a biodegradable polymer layer having no drug formed thereon. In order to achieve desired drug release behavior, the number and sequence of drug-loaded biodegradable polymer layers and biodegradable polymer layers having no drug may be variously adjusted. In the case where a plurality of drug-loaded biodegradable polymer layers is provided, there may be a plurality of polymers containing different drugs. Also, the drug release behavior may be controlled by adjusting the solubility or degradability of the biodegradable polymer layer depending on the kind of biodegradable polymer used.

In the present invention, the process of directly coating the surface of the suture with the polymer layer in a non-wet manner may be carried out by directly coating the surface of the suture with the drug-loaded biodegradable polymer layer in a non-wet manner, instead of the suture being immersed in the solution containing the drug. Specifically, the non-wet coating process may include a variety of coating processes, such as spraying, electrospraying, electrospinning, etc.

In the present invention, the drug may include but is not limited to one or more selected from the group consisting of ibuprofen; aspirin; choline salicylate; celecoxib; diclofenac sodium; misoprostol; diflunisal; etodolac; fenoprofen calcium; flurbiprofen; indomethacin; ketoprofen; magnesium salicylate; mefenamic acid; meloxicam; nabumetone; naproxen; naproxen sodium; oxaprozin; piroxicam; rofecoxib; salsalate; sodium salicylate; sulindac; tolmetin sodium; valdecoxib; docetaxel; paclitaxel; tamoxifen; anasterozole; imatinib; floxuridine; leuprolide; zoledronate; flutamide; doxorubicin; vincristine; gemcitabine; streptozocin; prednisolone; deflazacort; cyclophosphamide; azathioprine; methotrexate; cyclosporine; tacrolimus; anti fibrotic drugs such as pirfenidone, mitomycin (MMC), 5-fluorouracil (5-FU), Stratifin, acetylsalicylic acid (ASA), succinyl hydroxamates, selenocysteine, doxycycline, Osthole[7-methoxy-8-(3-methylpent-2-enyl) coumarin], genistein, Tranilast and Pseudolaric acid-B (PLAB); anti proliferative drugs such as tamoxifen (topical), halofuginone, vitamin C, nitrosylation derivatives of caspase-3, asiaticoside and 6-cyclohexyl-N-hydroxy-3-(1,2,4-oxadiazol-5-yl)hexanamides; hormones such as Relaxin; cytokines and monoclonal antibodies such as Exchange protein activated by cAMP 1 (Epacl), daclizumab and bevacizumab (Avastin); antiadhesive drugs such as perfluorocarbons, antisense oligodeoxynucleotide (ASODN), sodium carboxymethylcellulose (NaCMC) and poly(gamma-glutamic acid) (PGA); anti-ischemic compounds such as Necrox-5 and Necrox-7; amniotic membrane extracts; onion extracts; and garlic extracts. These drugs may be loaded alone or in combinations of two or more on a single polymer layer. Also, a plurality of layers respectively having different drugs may be provided. Also, a plurality of layers each having a plurality of drugs may be provided.

In the present invention, the biodegradable polymer may include but is not limited to polyester-based biodegradable polymers such as polylactide (PLA), polyglycolide (PGA) or a copolymer thereof such as poly(lactic-co-glycolic acid) (PLGA), polyorthoester, polyanhydride, polyamino acid, polyhydroxybutyric acid, polycaprolactone, polyalkylcarbonate, ethyl cellulose, chitosan, starch, guargum, gelatin, collagen, etc. Any polymer may be used so long as it is biodegradable. These biodegradable polymers may be used alone or in combinations of two or more.

In the present invention, the film including the polymer layer may be formed using electrospinning, solution casting or the like, but the present invention is not limited thereto.

In the present invention, the release of the drug may be controlled by adjusting the thickness of the polymer layer. Particularly in the case where the film is wound around the surface of the suture, drug release may be delayed for a desired period of time by adjusting the thickness of the biodegradable polymer layer having no drug (which is a barrier sheet), which is provided on the drug-loaded biodegradable polymer layer and functions as a drug diffusion barrier, so that sustained and extended drug release behavior is possible. Furthermore, drug release may be delayed for a desired period of time by adjusting the thickness of the coated polymer layer, the number of polymer layers, or the kind of polymer used, so that sustained and extended drug release behavior is possible. This principle may also be identically applied to the case where the surface of the suture is directly coated in a non-wet manner.

In addition, the present invention provides a method of manufacturing a suture, comprising 1) preparing a film including a drug-loaded biodegradable polymer layer (step 1), and 2) winding the film including the drug-loaded biodegradable polymer layer around the surface of a suture (step 2).

Also, the method may further comprise 3) applying heat or a solvent to the suture wound with the film, so that the wound film is adhered to the suture, after 2). Also, the wound film may be used as it is without being adhered to the suture.

In step 1), the film including the drug-loaded biodegradable polymer layer is prepared, which is a film including a polymer layer wherein a drug is loaded into a biodegradable polymer.

Specifically, step 1) may be performed by providing only the drug-loaded biodegradable polymer layer in the form of a film, or providing the drug-loaded biodegradable polymer layer in the form of a film and then additionally forming a biodegradable polymer layer having no drug on the drug-loaded biodegradable polymer layer.

The biodegradable polymer layer having no drug which is formed on the drug-loaded biodegradable polymer layer may function as a diffusion barrier for controlling the drug release thereby controlling the drug delivery period.

In step 2), the film including the drug-loaded biodegradable polymer layer is wound around the surface of the suture. That is, the film including the drug-loaded biodegradable polymer layer obtained in step 1) is wound around the surface of the suture.

In step 2), in the case where the film has an appropriate width, the film may be directly wound around the suture, or in the case where the film has a large width, it may be cut and then wound. As such, the width of the film may be set so that it will be easy to wind the film around the suture in light of the diameter of the suture. Generally, when the diameter of the suture is 300~400 μm, the width of the film may be 1.0~1.5 mm.

In step 2), the film may be wound once, twice or more as necessary. The drug release period may be controlled depending on the number of wound layers of the film. Also, in the case where the wound layers of the film is two or more, the winding direction of the film may be identical or different for each of the wound layers.

The kinds of drugs and biodegradable polymers that are usable are the same as in the description of the suture.

Also the process of forming the polymer layer may be performed using electrospinning mentioned in the description of the suture, but is not limited thereto.

In the method, 3) is a process of applying heat or a solvent to the suture wound with the film so as to adhere the film to the suture. That is, heat or the solvent is applied so that the film is physically and firmly adhered to the surface of the suture.

In the present invention, the wound film may be used as it is without being adhered to the suture, and thus 3) may be optionally performed and is not essential.

Particularly in the case where heat is applied to physically adhere the film and the suture, this process may be carried out in the temperature range from the glass transition temperature ($T_g$) of the biodegradable polymer to the melting point (Tm) of the drug. If the temperature of the heat is less than the above lower limit, the polymer does not undergo the glass transition procedure and there is no influence on its morphology, whereby the polymer may not be adhered to the surface of the suture. In contrast, if the temperature thereof is higher than the upper limit, the drug may be melted and thus the inherent structure and properties of the drug may be changed.

Also in the present invention, in the case where the solvent is added to physically adhere the film and the suture, the usable solvent may include but is not limited to dichloromethane, chloroform, dimethylformamide, tetrahydrofuran, acetone, methyl alcohol, ethyl alcohol, etc.

In addition, the present invention provides a method of manufacturing a suture, comprising 1) preparing a mixture comprising a drug and a biodegradable polymer (step 1) and 2) coating the surface of a suture with the mixture including the drug in a non-wet manner, thus forming a drug-loaded biodegradable polymer layer (step 2).

In the method, step 1) is a process of preparing the mixture comprising a drug and a biodegradable polymer. That is, the mixture in which the drug is dispersed in the biodegradable polymer is prepared.

In the method, step 2) is a process of coating the surface of the suture with the mixture including the drug in a non-wet manner, thus forming the drug-loaded biodegradable polymer layer.

Specifically, drug release may be delayed for a desired period by adjusting the thickness of the coated polymer layer, the number of polymer layers, and the kind of polymer in step 2), so that sustained and extended drug release behavior is possible.

The kinds of drugs and biodegradable polymers that are usable are the same as in the description of the suture. Also, the kind of the non-wet coating process is the same as in the description of the suture.

The following examples are set forth to illustrate but are not to be construed as limiting the present invention, and their purpose is to provide a better understanding of the present invention.

PREPARATION EXAMPLES 1~3

Preparation of Drug-Loaded Biodegradable Polymer Film (Drug Carrier)

A drug carrier was composed of a drug sheet having a loaded drug and a barrier sheet formed thereon to prevent the diffusion of the drug.

As shown in FIG. 1, the thickness of the drug sheet was maintained constant so that the amount of loaded drug was the same, and three kinds of drug carriers were prepared by adjusting the thickness of the barrier sheet. Specifically, Preparation Example 1 (DS) was composed exclusively of the drug sheet, Preparation Example 2 (DSB1) consisted of the drug sheet and the barrier sheet formed thereon using electrospinning for 100 min, and Preparation Example 3 (DSB2) was composed of the drug sheet and the barrier sheet formed thereon using electrospinning for 200 min.

The drug carriers were obtained using electrospinning. The specific preparation process was as follows.

In order to prepare the drug sheet, a biodegradable polymer, PLGA (i.v.=0.40 dl/g), was dissolved in a solvent mixture (3/1/1; v/v/v) comprising dichloromethane (DCM), tetrahydrofuran (THF) and dimethylformamide (DMF), thus obtaining a 30% (w/v) PLGA solution, in which ibuprofen as an anti-inflammatory drug was then dissolved in 10% (w/w) based on the PLGA.

The mixed solution of the biodegradable polymer and the drug was electrospun under the following conditions, giving a drug sheet.
  voltage: 15 kV
  collector rotation speed: 100 rpm
  tip to collector distance: 10 cm
  injection rate: 0.6 ml/h
  injection time: 100 min Subsequently, in order to prepare the barrier sheet, a 30% (w/v) PLGA solution was prepared in the same manner as above with the exception that ibuprofen was not added, after which electrospinning was additionally performed on the drug sheet using the PLGA solution thus forming a barrier sheet. The electrospinning conditions were the same as those given above, and only the injection time was adjusted to control the thickness of the barrier sheet.

The drug carriers thus obtained in the form of a sheet were uniformly cut at intervals of 1.5 mm (FIG. 1), thus preparing drug carrier strips.

EXAMPLES 1~3

Manufacture of Suture According to the Invention

Each of the drug carrier strips obtained in Preparation Examples 1 to 3 was wound around the surface of an intact original suture, thus three different kinds of sutures were manufactured according to the present invention.

Specifically, the suture was cut to 23 cm, and both ends thereof were securely clamped by a pair of grips having a spacing of 19 cm therebetween such that each both ends of the suture was gripped across a section of 2 cm from the end face, and the pair of grips were rotated by 22.5°, respectively, so as to cause the suture to be tightened.

Each of the drug carrier strips obtained in Preparation Examples 1 to 3 was closely wound around the suture without overlapping between adjacent windings of the drug carrier strip while the angle with respect to the axis of the suture was maintained at 30° (FIG. 2).

Both ends of the suture wound with the drug carrier were clamped together by a pair of grips having a spacing of 16 cm therebetween such that each of the both ends of the suture was gripped across a section of 1 cm from the end face, and then the pair of grips were rotated by 90°, respectively, so as to cause the suture wound with the drug carrier to be tightened (FIG. 3). This suture was placed in an oven at 47° C. in the temperature range from the glass transition temperature (TO of PLGA of 40~60° C. at which the morphology of PLGA may be changed to adhere PLGA to the surface of the suture, to the melting point (Tm) of ibuprofen of 75~78° C., and then heated for 1 hr, so that the drug carrier was physically adhered to the suture, thereby manufacturing the suture according to the invention.

TEST EXAMPLE 1

Adhesion of the Drug Carrier to the Suture According to the Invention

Figure 4A:
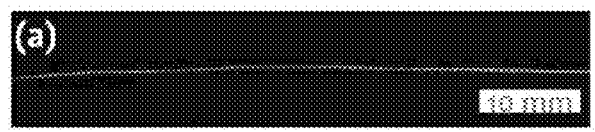
FIGS. 4A and 4B are optical images of an original suture and a DS suture coated with a film composed exclusively of a drug-loaded biodegradable polymer layer, respectively.
Figure 4B:

Because the PLGA of the drug carrier was heated in the temperature range close to $T_g$, the drug carrier and the suture were physically well attached while its morphology was slightly changed, which is observed in FIG. 4B which shows an optical image of the DS suture of Example 1. FIG. 4A is an optical image of the original suture, and FIG. 4B is an optical image of the DS suture.

Furthermore, in order to clearly observe the adhesion between the drug carrier and the original suture, the cross-section of the DS suture of Example 1 was observed with a SEM. The results are shown in FIGS. 4C and 4D, wherein the magnification of FIG. 4C is ×200, and the magnification of FIG. 4D is ×1000.

As shown in FIGS. 4A to 4D, the drug carrier was efficiently adhered to the surface of the suture.

TEST EXAMPLE 2

Amount of the Loaded Drug of the Suture According to the Invention

Each of the coated sutures of Examples 1 to 3 was cut to 4 cm and then added to 0.5 ml of DCM so that the PLGA of the drug carrier was completely dissolved, and 9.5 ml of acetonitrile (ACN) was added thereto.

The resulting solution was analyzed with high performance liquid chromatography (HPLC) (mobile phase: solvent mixture of 40 vol % of $H_2O$ and 60 vol % of ACN at pH 2.54 adjusted using o-phosphoric acid, column: C18, UV wavelength: 264 nm, flow rate: 0.8 ml/min, injection volume: 20 μl).

The coated sutures of 4 cm each had about 200.6 μg of ibuprofen.

TEST EXAMPLE 3

Drug Dissolution In Vitro of the Suture According to the Invention

The coated sutures of 4 cm were added to 2 ml of a buffer solution (pH 7.4), and the solution was then placed in an incubator at 37° C. and uniformly shaken at 125 rpm. 1 ml each of the solution was extracted at predetermined intervals, and it was replenished using 1 ml of another buffer solution. The extracted solution was analyzed at a wavelength of 264 nm using a UV spectrophotometer.

Figure 5:
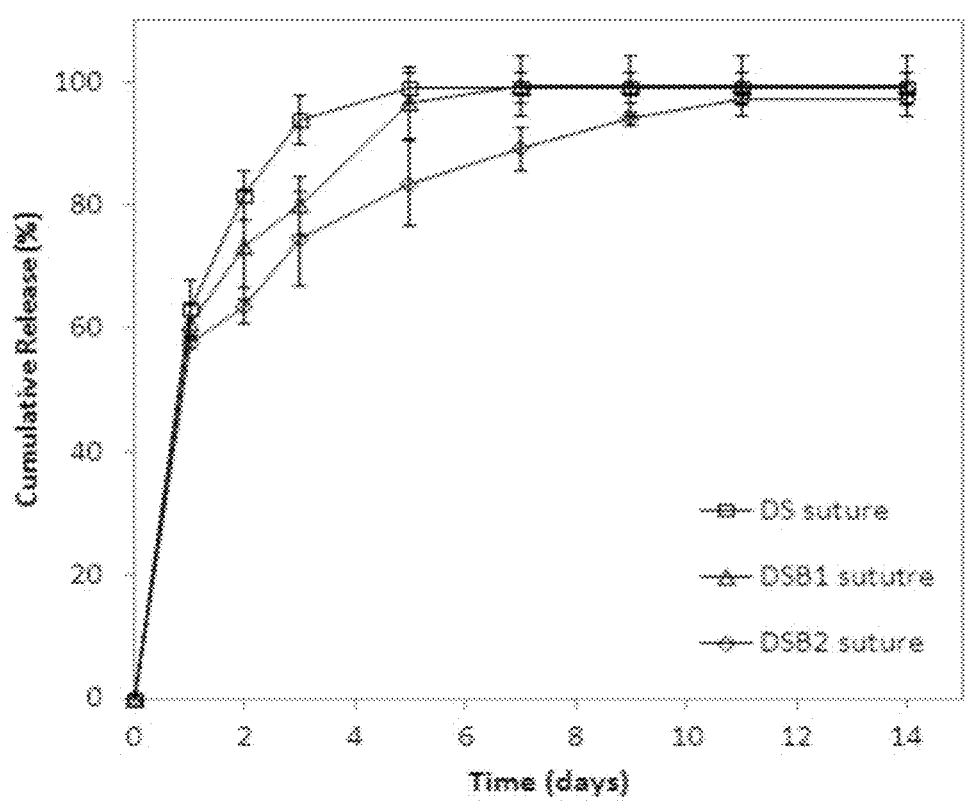
FIG. 5 shows the results of the in vitro drug release test of the suture according to the present invention, in which DS suture is a suture covered with the DS drug-loaded biodegradable polymer film, DSB1 suture is a suture covered with the DSB1 drug-loaded biodegradable polymer film, and DSB2 suture is a suture covered with the DSB2 drug-loaded biodegradable polymer film.

The in vitro drug release profiles are shown in FIG. 5.

As shown in FIG. 5, the drug delivery period was extended as the thickness of the barrier sheet increased.

On the first day of drug release, all three of the kinds of sutures had about 60% of initial burst, but the subsequent drug release rate was varied depending on the thickness of the barrier sheet. The drug was released, in the case of the DS suture, for 3 days, and in the case of the DSB1 suture, for 5 days, and in the case of DSB2 suture for 9 days.

TEST EXAMPLE 4

Mechanical Strength of the Suture According to the Invention

The mechanical strength of the original suture and three kinds of the coated sutures of Examples 1 to 3 was measured.

First, the spacing between a pair of grips of a force gauge was set to 15 cm, and both ends of the suture were clamped by the pair of grips, after which the coated suture was pulled at a rate of 200 mm/min. The length of the extended suture and the load value corresponding thereto were measured.

Figure 6:
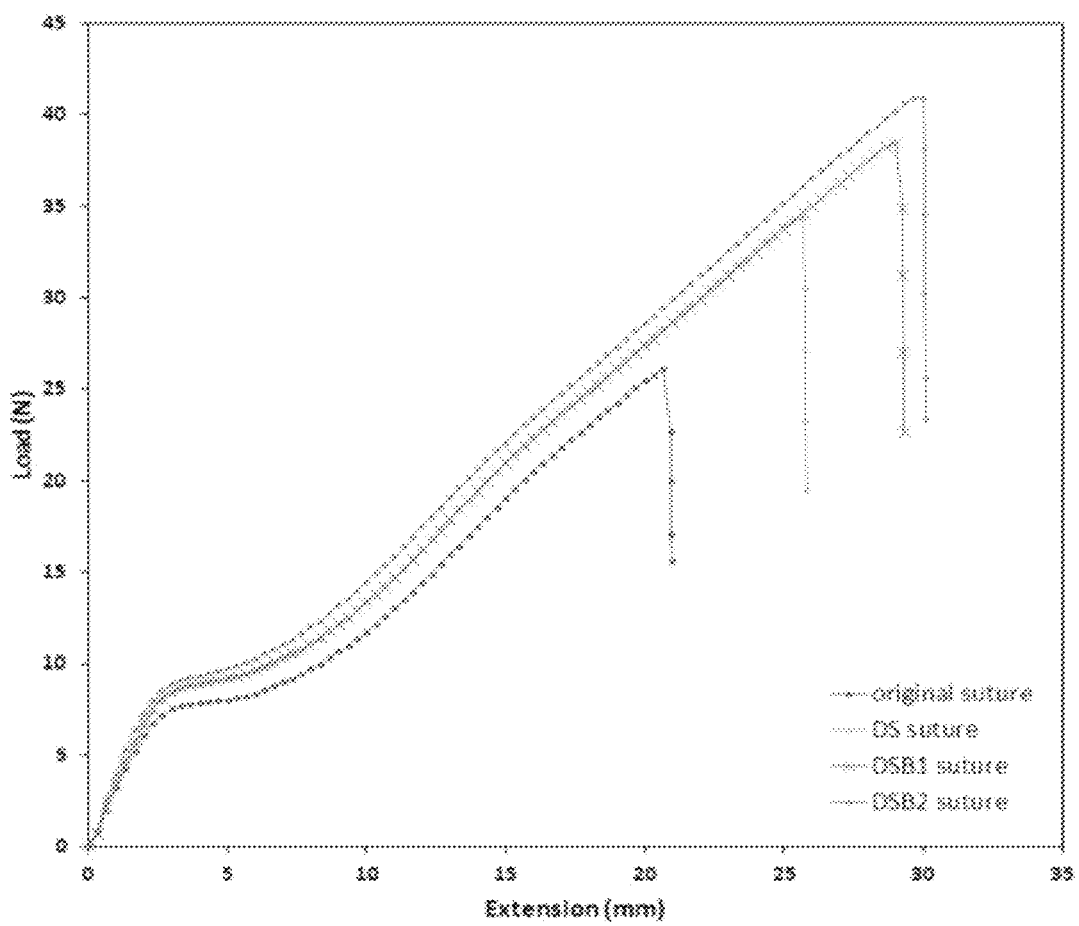
FIG. 6 shows the mechanical strength of the original suture and the coated sutures, in which DS suture is a suture covered with the DS drug-loaded biodegradable polymer film, DSB1 suture is a suture covered with the DSB1 drug-loaded biodegradable polymer film, and DSB2 suture is a suture covered with the DSB2 drug-loaded biodegradable polymer film.

FIG. 6 shows the extension versus the load of the original suture and three kinds of coated sutures.

The load value at which the suture was broken, namely, the failure load was larger in the coated sutures than in the original suture, which means that the coated sutures can endure a larger force. Particularly among the coated sutures, the failure load was increased in proportion to an increase in the thickness of the drug carrier wound around the original suture.

The mechanical strength of the original suture and three kinds of the coated sutures was measured and quantified. The results are shown in Table 1 below.

TABLE 1

| | Original suture | Ex. 1 (DS suture) | Ex. 2 (DSB1 suture) | Ex. 3 (DSB2 suture) |
|---|---|---|---|---|
| Strain at break | 21.44 ± 0.5664 | 25.44 ± 1.9115 | 26.67 ± 1.6998 | 26.44 ± 4.5652 |
| Failure load (N) | 26.63 ± 0.8188 | 35.44 ± 1.8641 | 37.91 ± 2.8051 | 40.16 ± 0.7635 |

As is apparent from Table 1, strain at the break and failure load were increased in all of Example 1 (DS suture), Example 2 (DSB1 suture) and Example 3 (DSB2 suture), compared to the original suture. Thus, the mechanical strength of the drug delivery sutures manufactured by the method of the present invention can be retained.

TEST EXAMPLE 5

Efficacy in Muscular Pain-Induced Rat Model 28 male SD rats having a weight of 250~300 g were bred under conditions of 21±1 C and 12-hr light/dark cycle for one week and then tested.

28 rats were randomly divided into four test groups each including 7 rats. Furthermore, normal rats having no incision were set as a control.

first group: after skin incision, the skin was sutured with a nylon suture.

second group: after skin incision, the quadriceps femoris muscle was artificially incised, after which the wound was sutured with an absorbable suture having no drug and the skin was sutured with a nylon suture.

third group: after skin incision, the quadriceps femoris muscle was artificially incised, after which the wound was sutured with the absorbable suture (DS suture) of Example 1 including the drug and the PLGA and the skin was sutured with a nylon suture (i.e. the muscle was sutured with the suture having the drug delivery time of 3 days).

fourth group: after skin incision, the quadriceps femoris muscle was artificially incised, after which the wound was sutured with the absorbable suture (DSB2 suture) of Example 3 having the drug-loaded PLGA layer and the PLGA layer having no drug and the skin was sutured with a nylon suture (i.e. the muscle was sutured with the suture having the drug delivery period of 9 days)

After the above operation, rearing counts were measured at regular intervals for two weeks using a photobeam sensor (Photo beam & Video motion analysis system, In Electronics Design, Korea) to analyze the motility so as to evaluate the degree of pain. Upon statistical treatment, analysis was conducted based on the first group.

Figure 7:
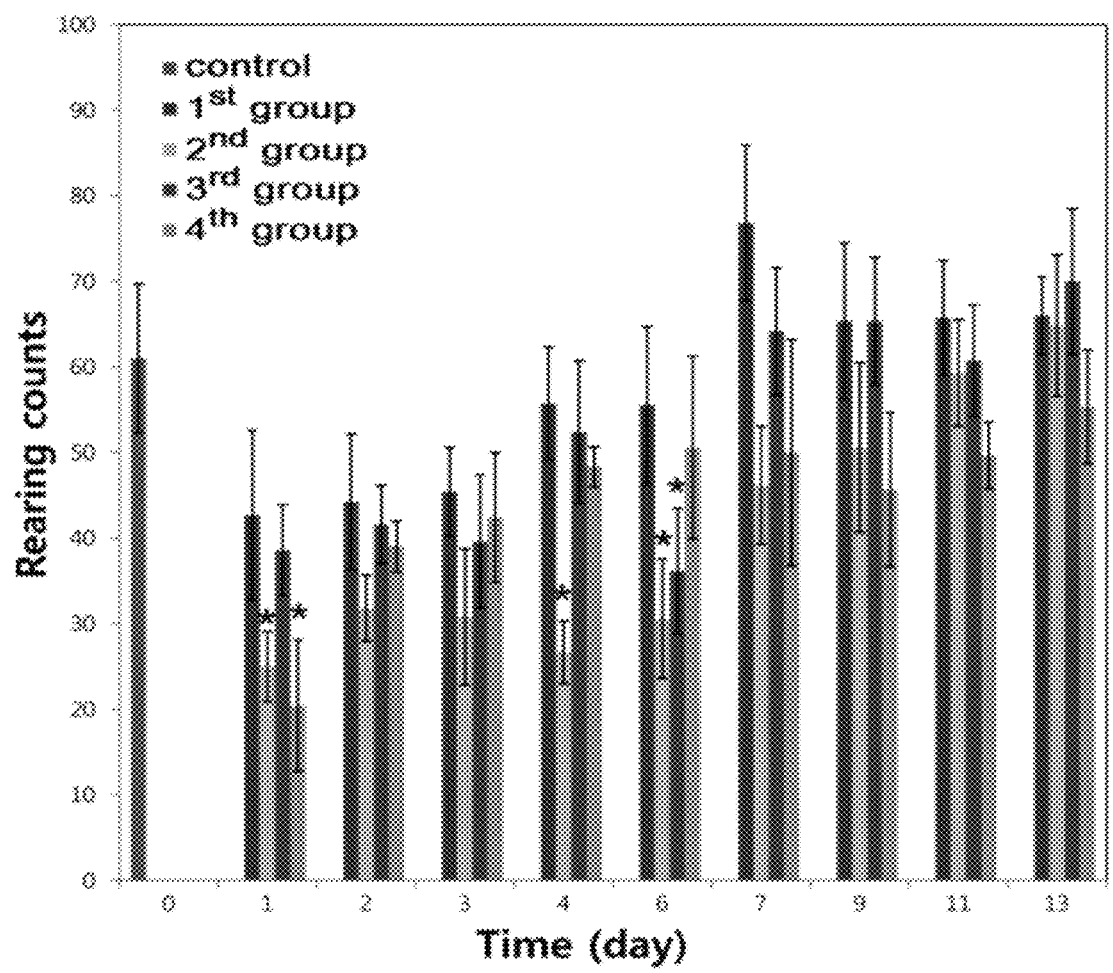
FIG. 7 is a graph showing the efficacy of pain-relieving drug-loaded sutures in a muscular pain-induced rat model.

The results are shown in FIG. 7.

On the first day, the group in which the wound was sutured with the suture having no drug (the second group) felt pain, compared to the group to which only the skin incision was applied (the first group). However, the group in which the wound was sutured with the DS suture coated with the drug (the third group) exhibited the pain relief effect of ibuprofen. Therefore, it was not statistically significant with the first group and felt a comparatively small amount of pain. In the case of the group in which the wound was sutured with the DSB2 suture coated with the drug and PLGA (the fourth group), the drug was slowly released due to the effects of PLGA, and thus on the first day, the fourth group was statistically significant with the first group and felt pain.

On the second and third days, there was no obvious statistical significance between the second group and the first group but the second group manifested a low average value and seemed to feel pain. However, the third and fourth groups exhibited the rearing counts similar to those of the first group because of the drug effects and did not feel a great amount of pain. This tendency continued to the fourth day, where there was a statistically significant difference between the second group and the first group.

On the sixth day, for the third group, almost all of drug was already released and thus, the third group started to feel pain again, which was statistically confirmed. However, the fourth group in which the drug release rate was delayed by PLGA and thus, drug was still released on the sixth day, did not feel a large amount of pain. The second group was not recovered yet and was still in pain.

All the groups were fully recovered after the seventh day. On the seventh day, the difference between the fourth group and the first group was statistically significant. However, considering the fact that the average value of the first group on that day was remarkably high, the fourth group was considered to be recovered normally.

In consequence, drug delivery is effectively carried out in the case where only the drug is applied or both the drug and the PLGA are applied, advantageously affecting pain relief. Pain can be undesirably induced again if the drug-release period is shorter than the period of healing. However, a biodegradable polymer, such as PLGA, can further control the drug release rate to resolve this problem.

As described hereinbefore, the present invention provides a suture comprising a drug-loaded polymer layer and a method of manufacturing the same. According to the present invention, the suture can be manufactured by preparing a film including a drug-loaded biodegradable polymer layer, and covering the film including the drug-loaded biodegradable polymer layer around the surface of a suture or directly coating the surface of a suture with the drug-loaded biodegradable polymer layer in a non-wet manner, and thus can achieve effective drug delivery without having decreased mechanical strength.

Although the embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A suture, comprising a suture and a film disposed in a winding manner around a surface of the suture, wherein the film comprises a drug-loaded biodegradable polymer layer in a form of a sheet, and the drug is present in a mixture with the biodegradable polymer within the drug-loaded polymer layer.

2. The suture of claim 1, wherein the film further comprises a biodegradable polymer layer having no drug, which is provided on the drug-loaded biodegradable polymer layer and functions as a drug diffusion barrier.

3. The suture of claim 1, wherein the drug is one or more of ibuprofen, aspirin, choline salicylate, celecoxib, diclofenac sodium, misoprostol, diflunisal, etodolac, fenoprofen calcium, flurbiprofen, indomethacin, ketoprofen, magnesium salicylate, mefenamic acid, meloxicam, nabumetone, naproxen, naproxen sodium, oxaprozin, piroxicam, rofecoxib, salsalate, sodium salicylate, sulindac, tolmetin sodium, valdecoxib, docetaxel, paclitaxel, tamoxifen, anasterozole, imatinib, floxuridine, leuprolide, zoledronate, flutamide, doxorubicin, vincristine, gemcitabine, streptozocin, prednisolone, deflazacort, cyclophosphamide, azathioprine, methotrexate, cyclosporine, tacrolimus, pirfenidone, mitomycin, 5-fluorouracil, Stratifin, acetylsalicylic acid, succinyl hydroxamates, selenocysteine, doxycycline, Osthole, genistein, Tranilast, Pseudolaric acid-B, tamoxifen(topical), halofuginone, vitamin C, nitrosylation derivatives of caspase-3, asiaticoside, 6-cyclohexyl-N-hydroxy-3-(1,2,4-oxadiazol-5-yl)hexanamides, Relaxin, Exchange protein activated by cAMP 1, daclizumab, bevacizumab, perfluorocarbons, antisense oligodeoxynucleotide, sodium carboxymethylcellulose, poly (gamma-glutamic acid), Necrox-5, Necrox-7, amniotic membrane extracts, onion extracts or garlic extracts.

4. The suture of claim 1, wherein the biodegradable polymer is polylactide (PLA), polyglycolide (PGA), poly(lactic-co-glycolic acid) (PLGA), polyorthoester, polyanhydride, polyamino acid, polyhydroxybutyric acid, polycaprolactone, polyalkylcarbonate, ethyl cellulose, chitosan, starch, guargum, gelatin, or collagen.

5. The suture of claim 1, wherein the film is adhered to the suture by treatment of heat or a solvent and wherein the solvent is selected from the group consisting of dichloromethane, chloroform, dimethylformamide, tetrahydrofuran, acetone, methylalcohol, ethylalcohol and combinations thereof.

6. A method of manufacturing a suture comprising the steps of:
   1) preparing a film including a drug-loaded biodegradable polymer layer in a form of a sheet; and
   2) winding the film including the drug-loaded biodegradable polymer layer around a surface of a suture.

7. The method of claim 6, wherein preparing the film including the drug-loaded biodegradable polymer layer in step 1) is performed by providing only a drug-loaded biodegradable polymer layer in film form, or by providing a drug-loaded biodegradable polymer layer in film form and then forming a biodegradable polymer layer having no drug on the drug-loaded biodegradable polymer layer.

8. The method of claim 6, further comprising applying heat or a solvent to the suture wound with the film so that the wound film is adhered to the suture, after step 2).

9. The method of claim 6, wherein the drug is one or more of ibuprofen, aspirin, choline salicylate, celecoxib, diclofenac sodium, misoprostol, diflunisal, etodolac, fenoprofen calcium, flurbiprofen, indomethacin, ketoprofen, magnesium salicylate, mefenamic acid, meloxicam, nabumetone, naproxen, naproxen sodium, oxaprozin, piroxicam, rofecoxib, salsalate, sodium salicylate, sulindac, tolmetin sodium, valdecoxib, docetaxel, paclitaxel, tamoxifen, anasterozole, imatinib, floxuridine, leuprolide, zoledronate, flutamide, doxorubicin, vincristine, gemcitabine, streptozocin, prednisolone, deflazacort, cyclophosphamide, azathioprine, methotrexate, cyclosporine, tacrolimus, pirfenidone, mitomycin, 5-fluorouracil, Stratifin, acetylsalicylic acid, succinyl hydroxamates, selenocysteine, doxycycline, Osthole, genistein, Tranilast, Pseudolaric acid-B, tamoxifen(topical), halofuginone, vitamin C, nitrosylation derivatives of caspase-3, asiaticoside, 6-cyclohexyl-N-hydroxy-3-(1,2,4-oxadiazol-5-yl)hexanamides, Relaxin, Exchange protein activated by cAMP 1, daclizumab, bevacizumab, perfluorocarbons, antisense oligodeoxynucleotide, sodium carboxymethylcellulose, poly (gamma-glutamic acid), Necrox-5, Necrox-7, amniotic membrane extracts, onion extracts or garlic extracts.

10. The method of claim 6, wherein the biodegradable polymer is polylactide (PLA), polyglycolide (PGA), poly (lactic-co-glycolic acid) (PLGA), polyorthoester, polyanhydride, polyamino acid, polyhydroxybutyric acid, polycaprolactone, polyalkylcarbonate, ethyl cellulose, chitosan, starch, guargum, gelatin, or collagen.

11. The method of claim 6, wherein the film including the polymer layer is formed using electrospinning or solution casting.

12. The method of claim 8, wherein the solvent is dichloromethane, chloroform, dimethylformamide, tetrahydrofuran, acetone, methylalcohol, ethylalcohol or combinations thereof.

* * * * *